United States Patent
Cushner et al.

(10) Patent No.: US 9,237,841 B2
(45) Date of Patent: Jan. 19, 2016

(54) ADJUSTABLE BITE BLOCKS

(71) Applicant: Bracco Diagnostics Inc., Monroe Township, NJ (US)

(72) Inventors: Jeffrey B. Cushner, Woodmere, NY (US); Ali H. Duman, Melville, NY (US); Christopher R. Stebbins, Huntington Station, NY (US); Kenneth E. Wolcott, Centerport, NY (US)

(73) Assignee: Bracco Diagnostics Inc., Monroe Township, NJ (US)

( * ) Notice: Subject to any disclaimer, the term of this patent is extended or adjusted under 35 U.S.C. 154(b) by 56 days.

(21) Appl. No.: 14/208,400

(22) Filed: Mar. 13, 2014

(65) Prior Publication Data
US 2014/0275803 A1 Sep. 18, 2014

Related U.S. Application Data

(60) Provisional application No. 61/780,137, filed on Mar. 13, 2013.

(51) Int. Cl.
*A61B 1/32* (2006.01)
*A61B 1/24* (2006.01)
*A61M 16/04* (2006.01)

(52) U.S. Cl.
CPC ... *A61B 1/24* (2013.01); *A61B 1/32* (2013.01); *A61M 16/0493* (2014.02)

(58) Field of Classification Search
CPC combination set(s) only.
See application file for complete search history.

(56) References Cited

U.S. PATENT DOCUMENTS

| | | | |
|---|---|---|---|
| 2,823,455 A | 2/1958 | Sprague |
| 4,167,814 A | 9/1979 | Schubert |
| 4,304,227 A | 12/1981 | Samelson |
| D283,158 S | 3/1986 | Jackson |
| 4,640,273 A | 2/1987 | Greene et al. |
| 4,887,965 A | 12/1989 | Fox |
| 4,975,057 A | 12/1990 | Dyfvermark |
| 5,069,206 A | 12/1991 | Crosbie |
| 5,174,284 A | 12/1992 | Jackson |
| 5,466,153 A | 11/1995 | Poindexter |

(Continued)

FOREIGN PATENT DOCUMENTS

| | | |
|---|---|---|
| EP | 1 153 594 A2 | 11/2001 |
| FR | 2711320 | 4/1995 |
| GB | 183301 | 7/1922 |

OTHER PUBLICATIONS

International Search Report and Written Opinion for Application No. PCT/US2014/025548 dated Jul. 16, 2014.

*Primary Examiner* — Sameh Boles
(74) *Attorney, Agent, or Firm* — Alston & Bird LLP

(57) ABSTRACT

Embodiments of the present invention relate to an adjustable bite block for positioning within a person's mouth and maintaining the mouth in an open position. The adjustable bite block comprising at least one band of curved material comprising a first portion and a second portion. The first and second portions configured to be coupled to one another so as to define a closed loop with an opening defined therethrough, wherein the first and second portions are further configured to be selectively adjusted relative to one another so as to adjust a radial dimension of the loop, and wherein the band is configured to be positioned within the person's mouth such that at least a portion of the loop maintains the person's mouth in an open position. Embodiments of the adjustable bite block may use snap tabs spaced along the band or a ratchet mechanism for adjustment of the radial dimension.

6 Claims, 19 Drawing Sheets

(56) References Cited

U.S. PATENT DOCUMENTS

| | | |
|---|---|---|
| 5,570,704 A | 11/1996 | Buzzard et al. |
| 5,588,836 A | 12/1996 | Landis et al. |
| 5,655,519 A | 8/1997 | Alfery |
| 5,730,599 A | 3/1998 | Pak |
| 5,733,121 A | 3/1998 | Goode |
| 5,890,899 A | 4/1999 | Sclafani |
| 6,200,133 B1 | 3/2001 | Kittelsen |
| 6,241,521 B1 | 6/2001 | Garrison |
| 6,244,866 B1 | 6/2001 | Campbell |
| 6,652,276 B2 | 11/2003 | Fischer et al. |
| 6,655,960 B2 | 12/2003 | Fischer |
| 6,983,752 B2 | 1/2006 | Garabadian |
| D564,658 S | 3/2008 | Anderson |
| 7,442,040 B2 | 10/2008 | Kuo |
| 7,568,484 B2 | 8/2009 | Bierman et al. |
| 2005/0239017 A1 | 10/2005 | Lim |
| 2005/0239018 A1 | 10/2005 | Green et al. |
| 2006/0110705 A1 | 5/2006 | Jensen et al. |
| 2007/0148619 A1 | 6/2007 | Anderson |
| 2007/0218422 A1 | 9/2007 | Ehrenfeld |
| 2008/0153057 A1 | 6/2008 | Baldwin |
| 2008/0295849 A1 | 12/2008 | Reynolds, II et al. |
| 2009/0050161 A1 | 2/2009 | Burdumy |
| 2009/0308403 A1 | 12/2009 | Roettger et al. |
| 2011/0017220 A1* | 1/2011 | Lindsay ............ A61F 5/566 128/848 |

* cited by examiner

US 9,237,841 B2

ADJUSTABLE BITE BLOCKS

CROSS-REFERENCE TO RELATED APPLICATIONS

This application claims the benefit of U.S. Provisional Application No. 61/780,137 entitled "Adjustable Bite Blocks," filed Mar. 13, 2013, the contents of which are incorporated herein in their entirety.

FIELD

Embodiments of the present invention discussed herein are related to an oral apparatus for dentistry and other medical procedures, and more particularly to an oral apparatus for maintaining a person's mouth open during such dentistry and medical procedures.

BACKGROUND

Often, dental and medical procedures, like endoscopy, require medical instruments to be passed orally, through a person's mouth. Some patient's may accidentally or otherwise close their mouths during the procedure which can harm the patient or ruin the medical instrument. In order to maintain a person's mouth open during a procedure, often an oral apparatus is placed in the person's mouth. However, many patients have different size mouths, and the oral apparatus placed in the person's mouth may be uncomfortable or difficult for the doctor to work around with the medical instrument. Therefore, improvements are needed so that an oral apparatus will fit properly in different size mouths and provide proper exposure for medical instruments to be passed orally.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 6:
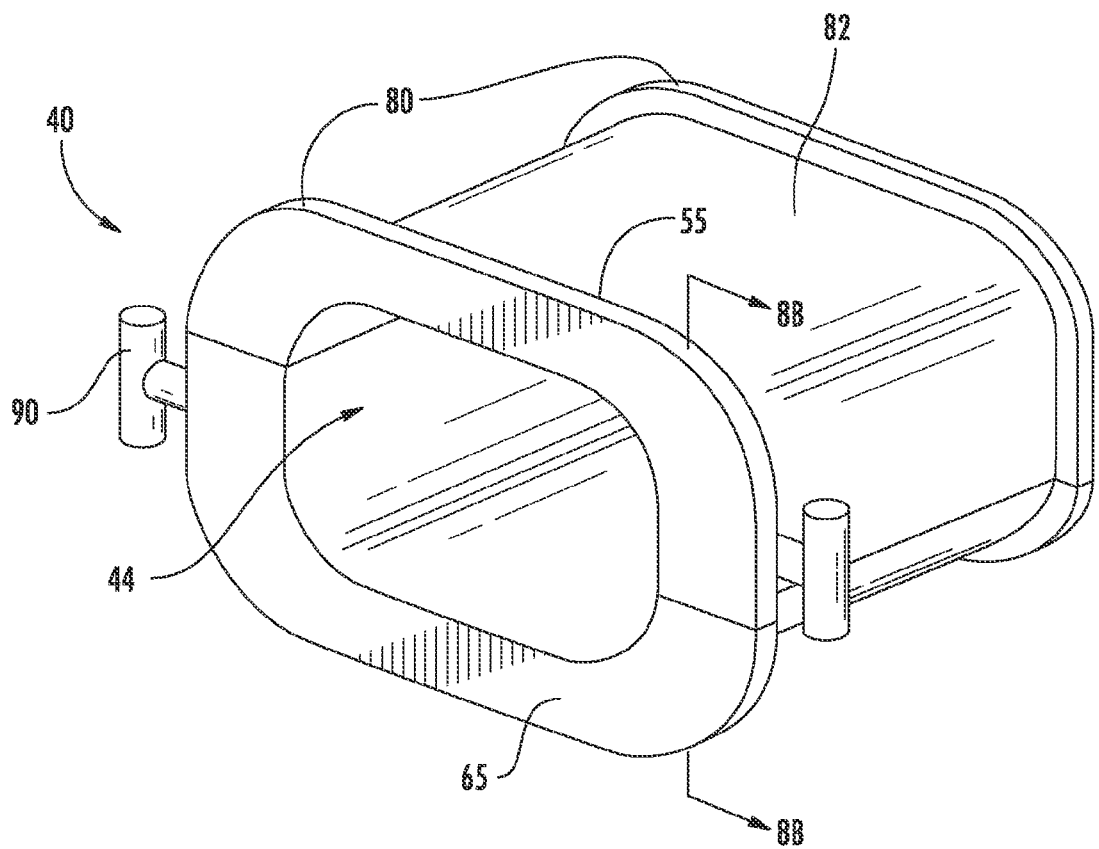
FIG. 6 is a perspective view of an oral appliance for maintaining a person's mouth in the open position, wherein the oral appliance is an adjustable bite block, according to one embodiment of the present invention.
Figure 7:
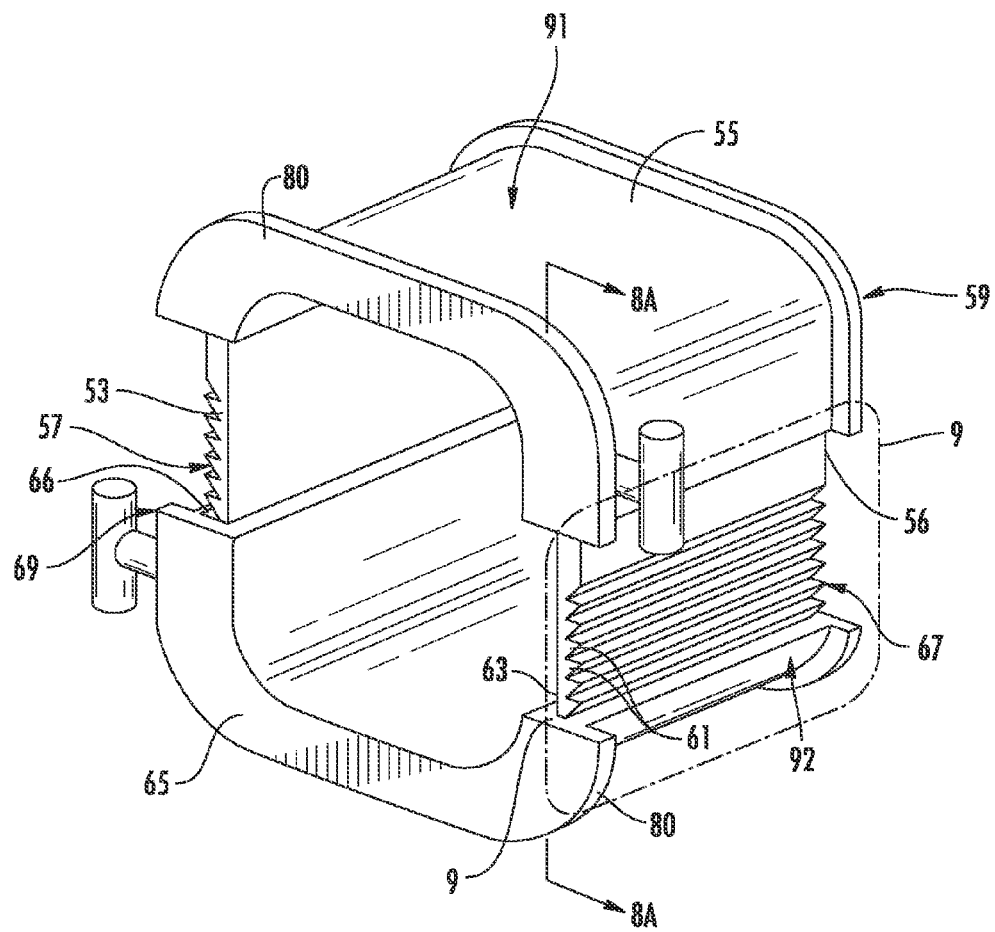
FIG. 7 is a perspective view of the adjustable bite block shown in FIG. 6 disposed in a disconnected configuration, according to one embodiment of the present invention.
Figure 8A:
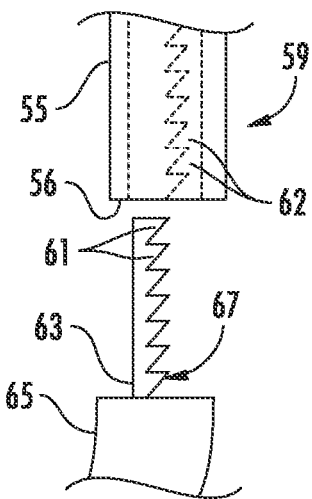
FIG. 8A is a detailed cross-sectional view taken along line 8A in FIG. 7 of the adjustable bite block shown in FIG. 6, wherein the adjustable bite block is disposed in a disconnected configuration, according to one embodiment of the present invention.
Figure 8B:
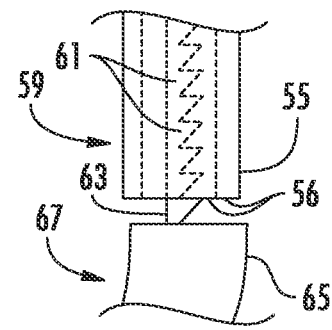
Figure 9:
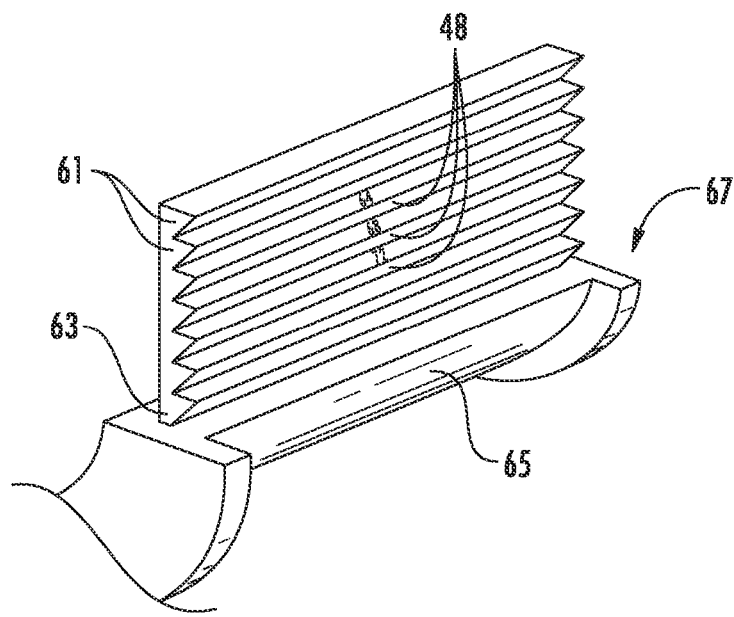
Figure 10:
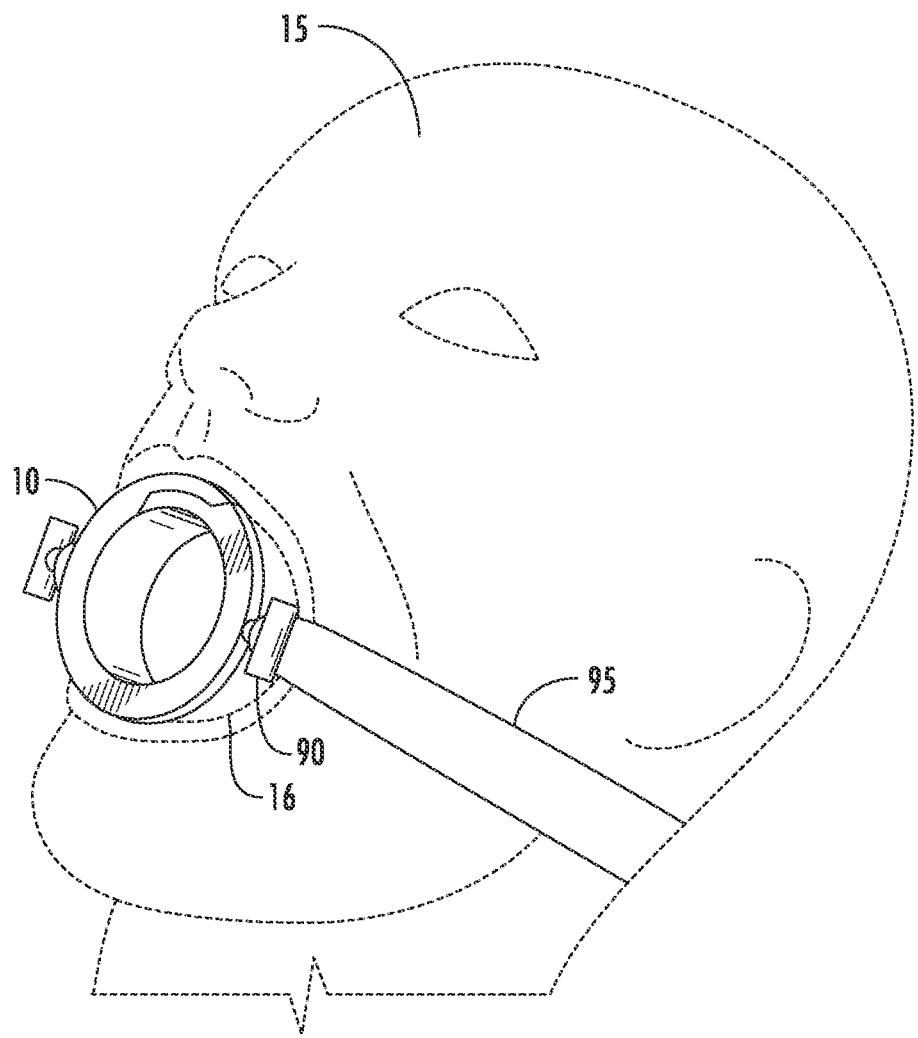
Figure 11:
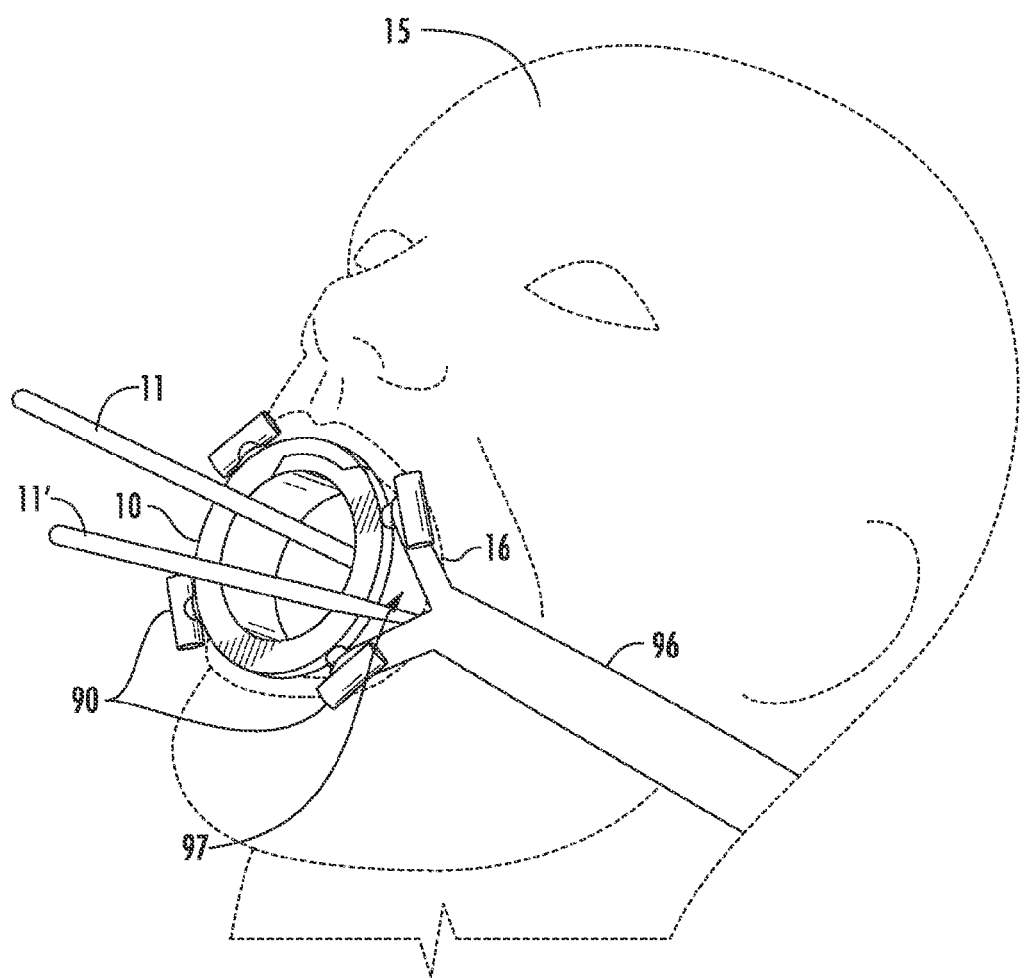
Figure 12:
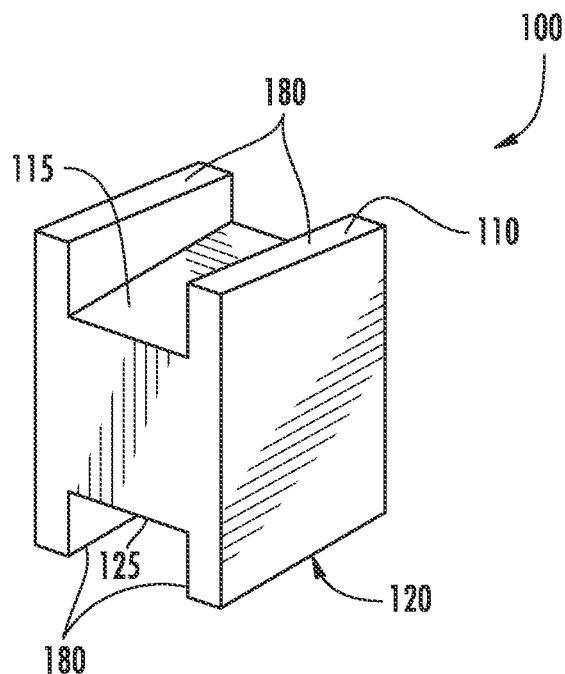
Figure 13:
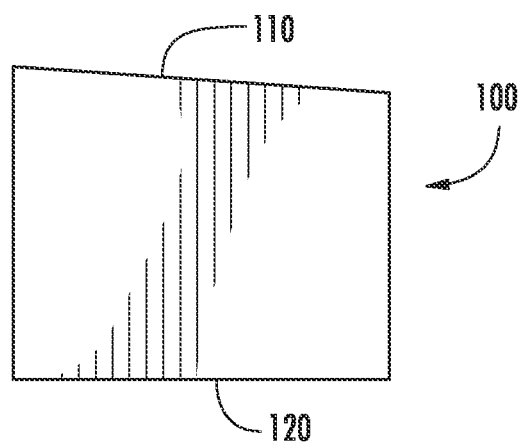
Figure 14:
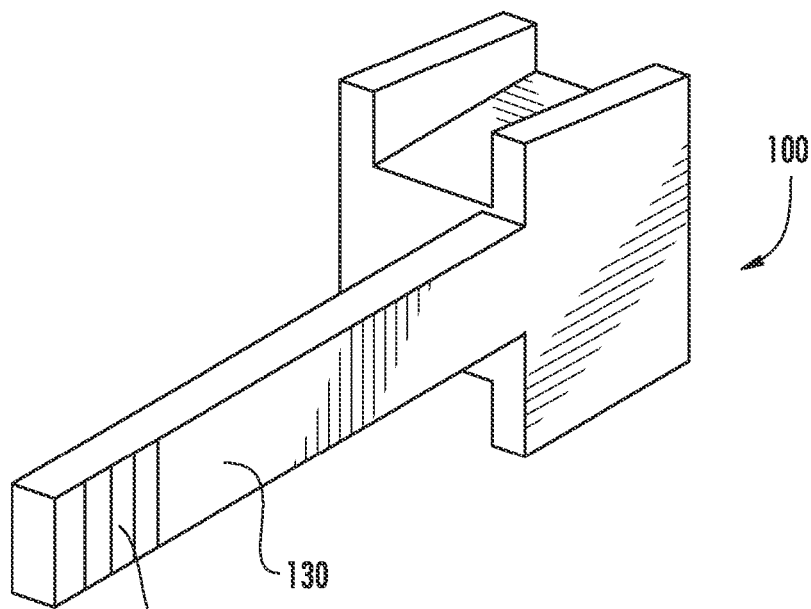
Figure 15:
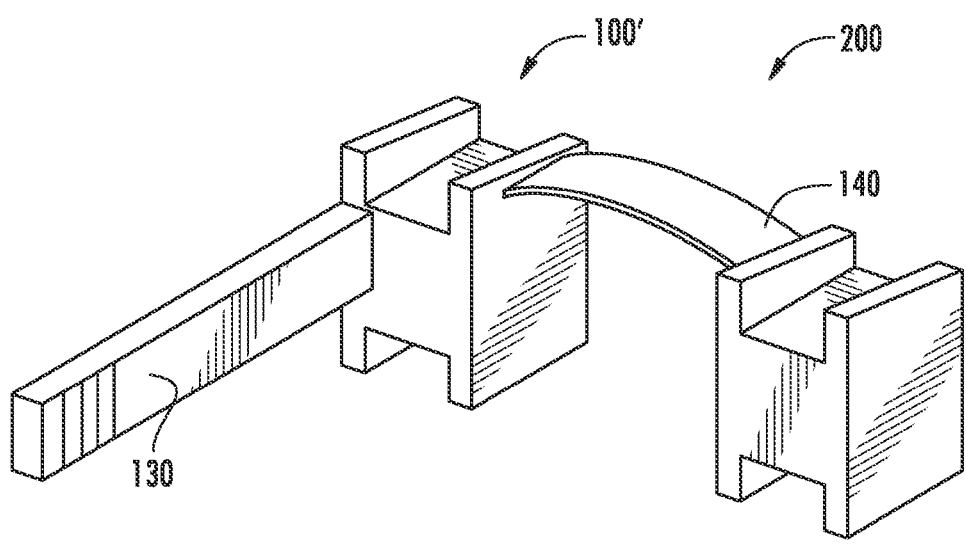
Figure 16:
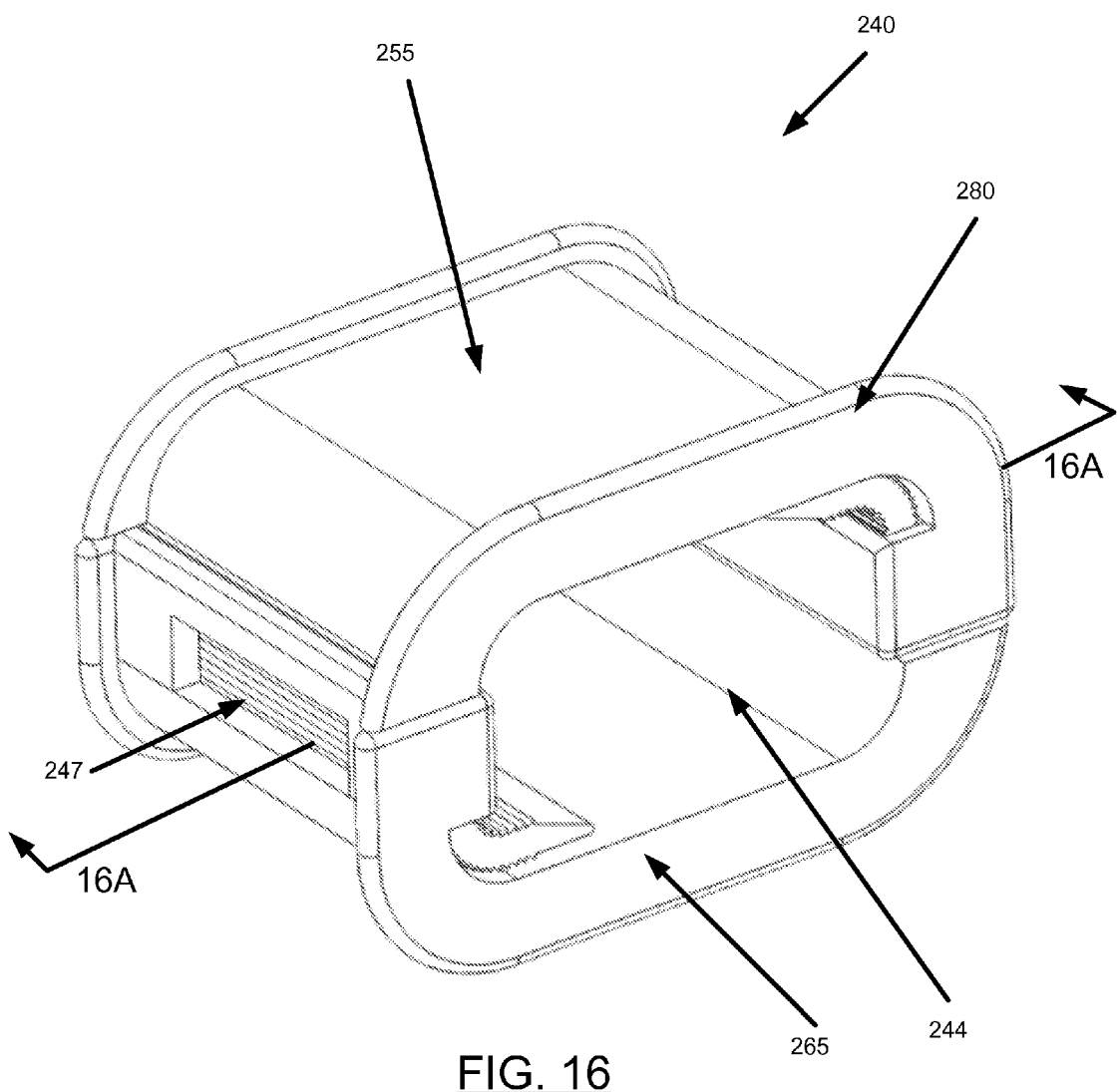
Figure 16A:
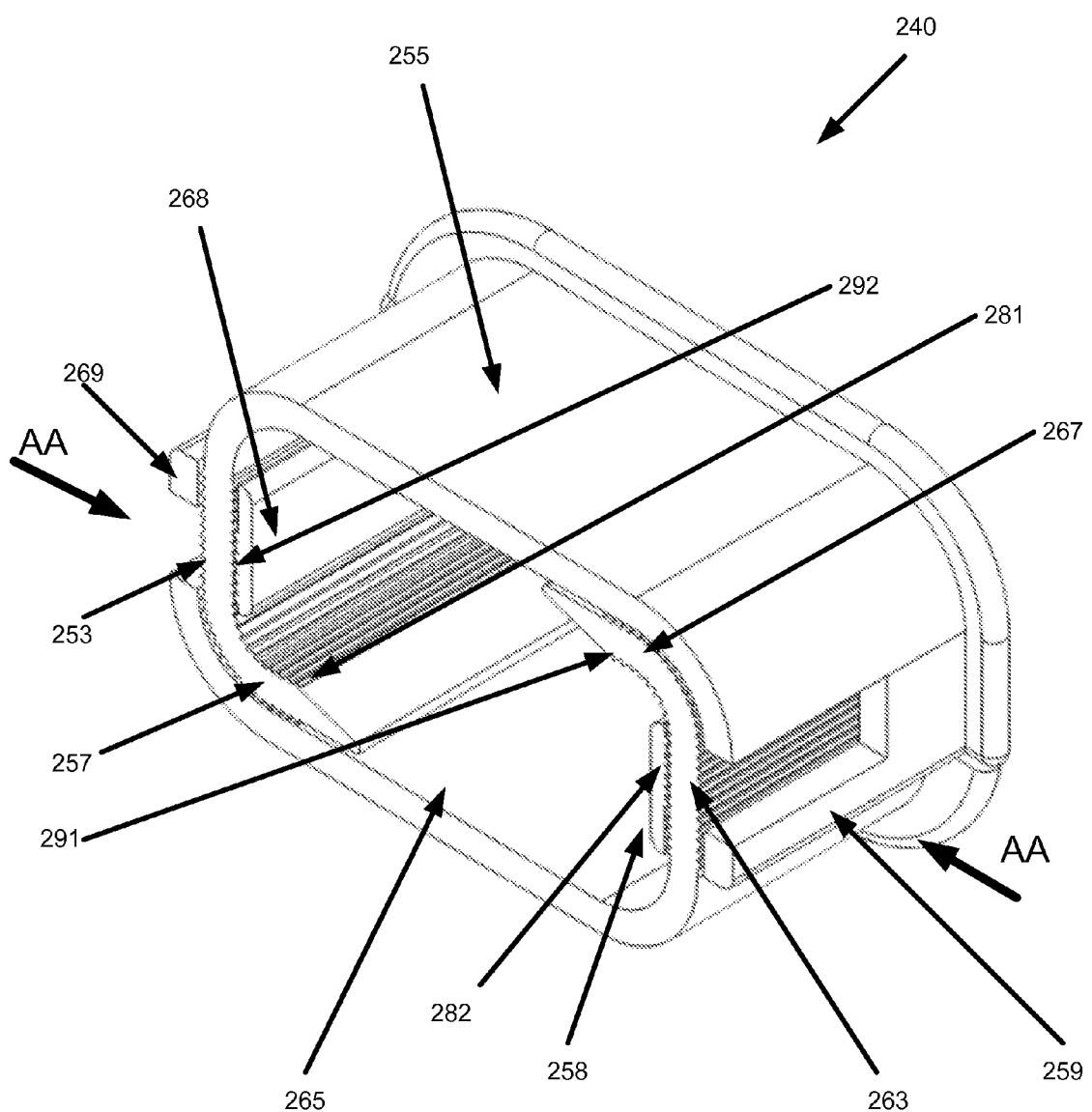
Figure 17:
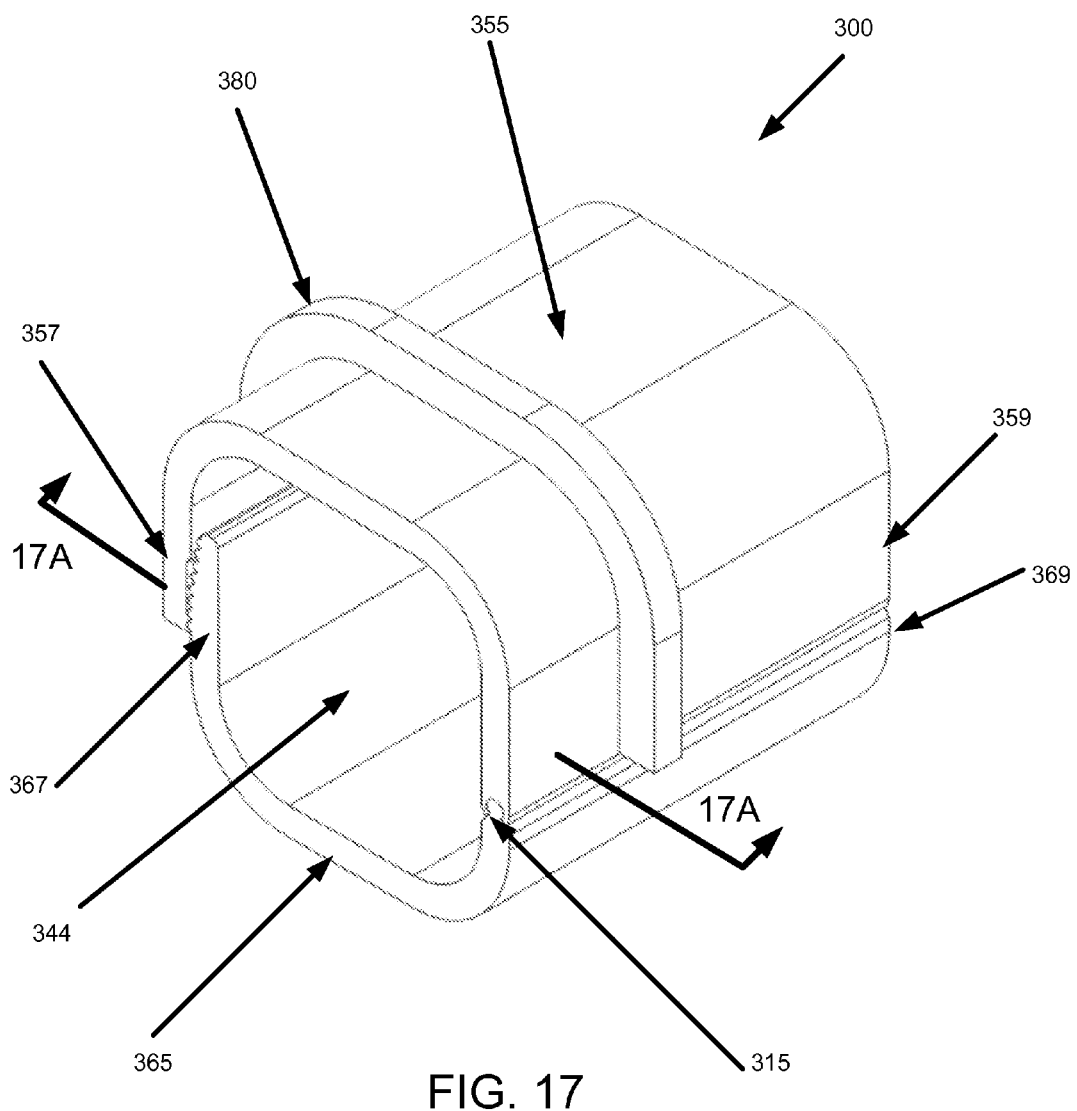
Figure 17A:
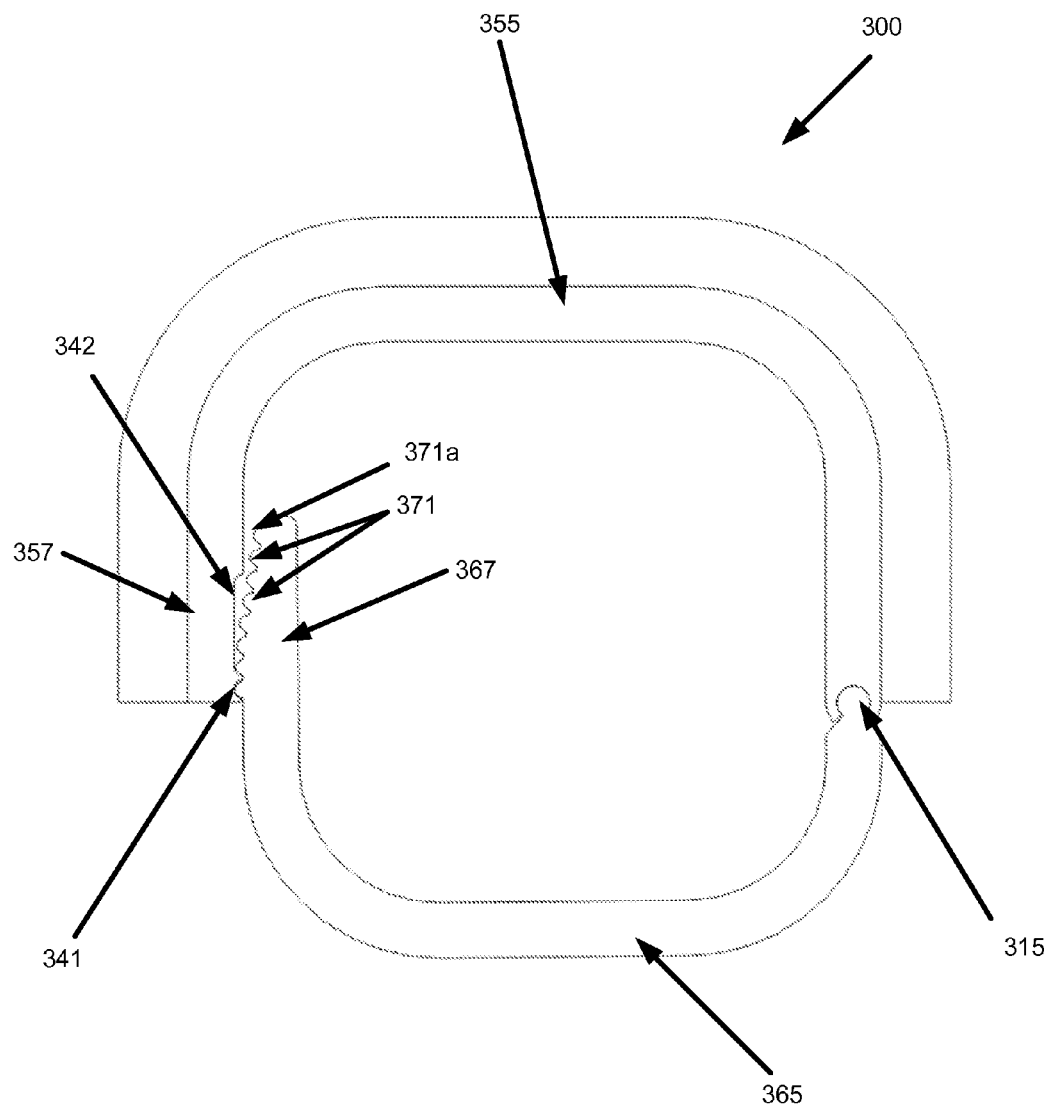
Figure 18:
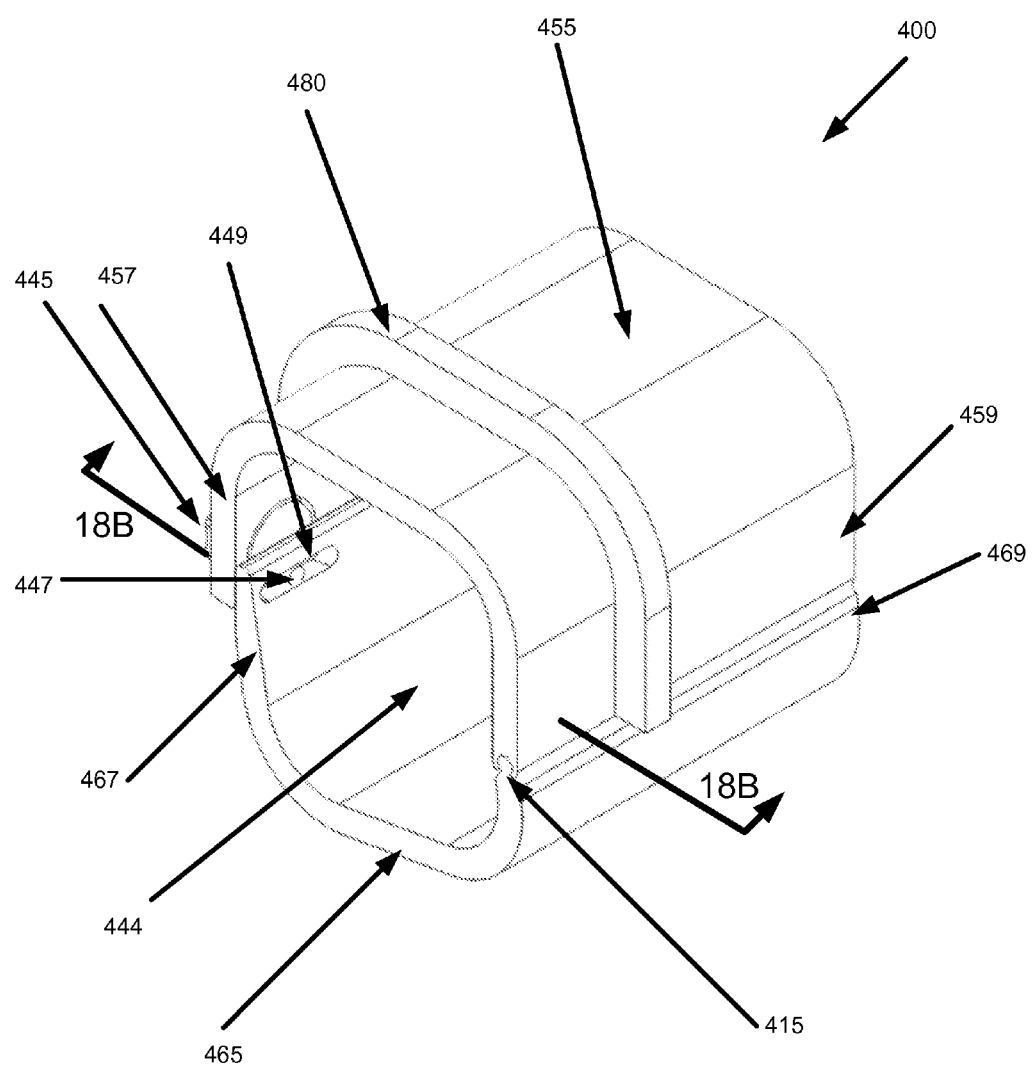
Figure 18A:
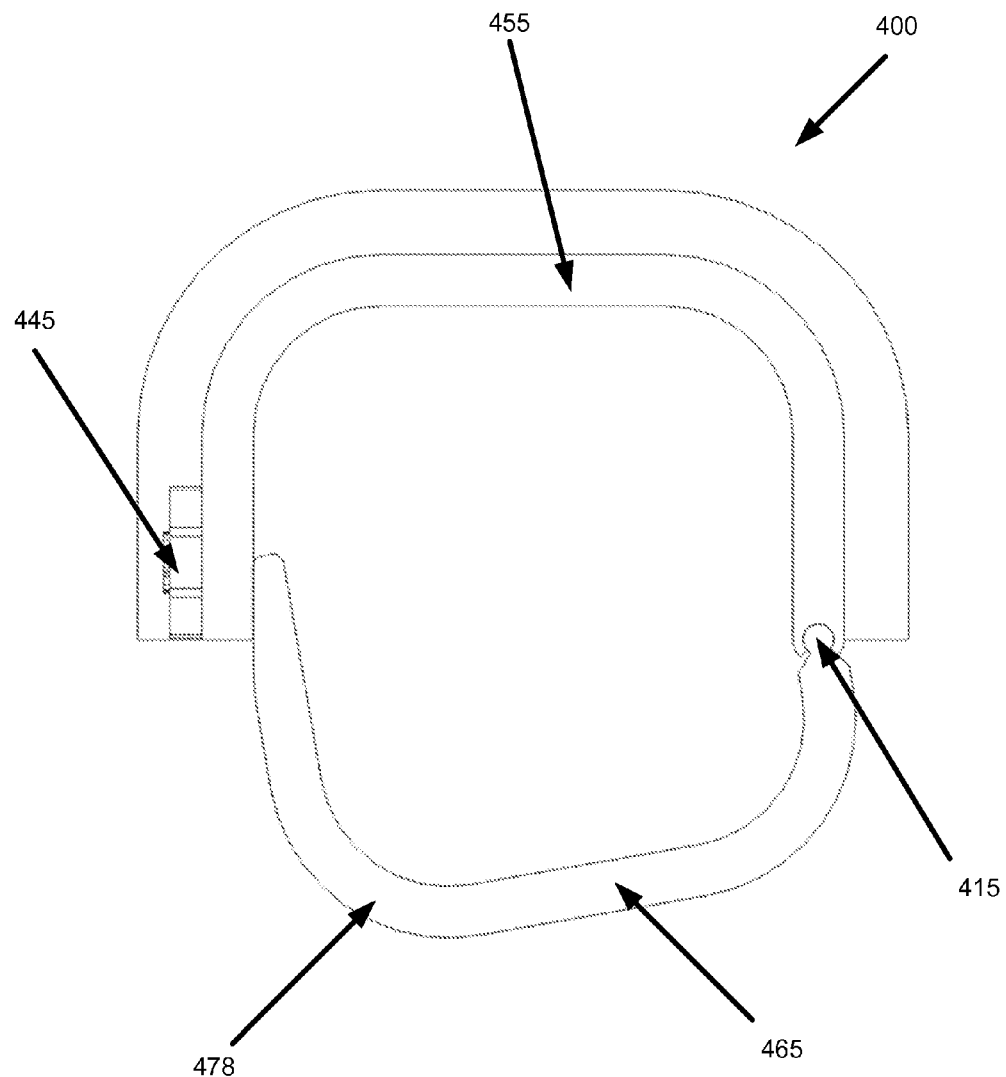
Figure 18B:
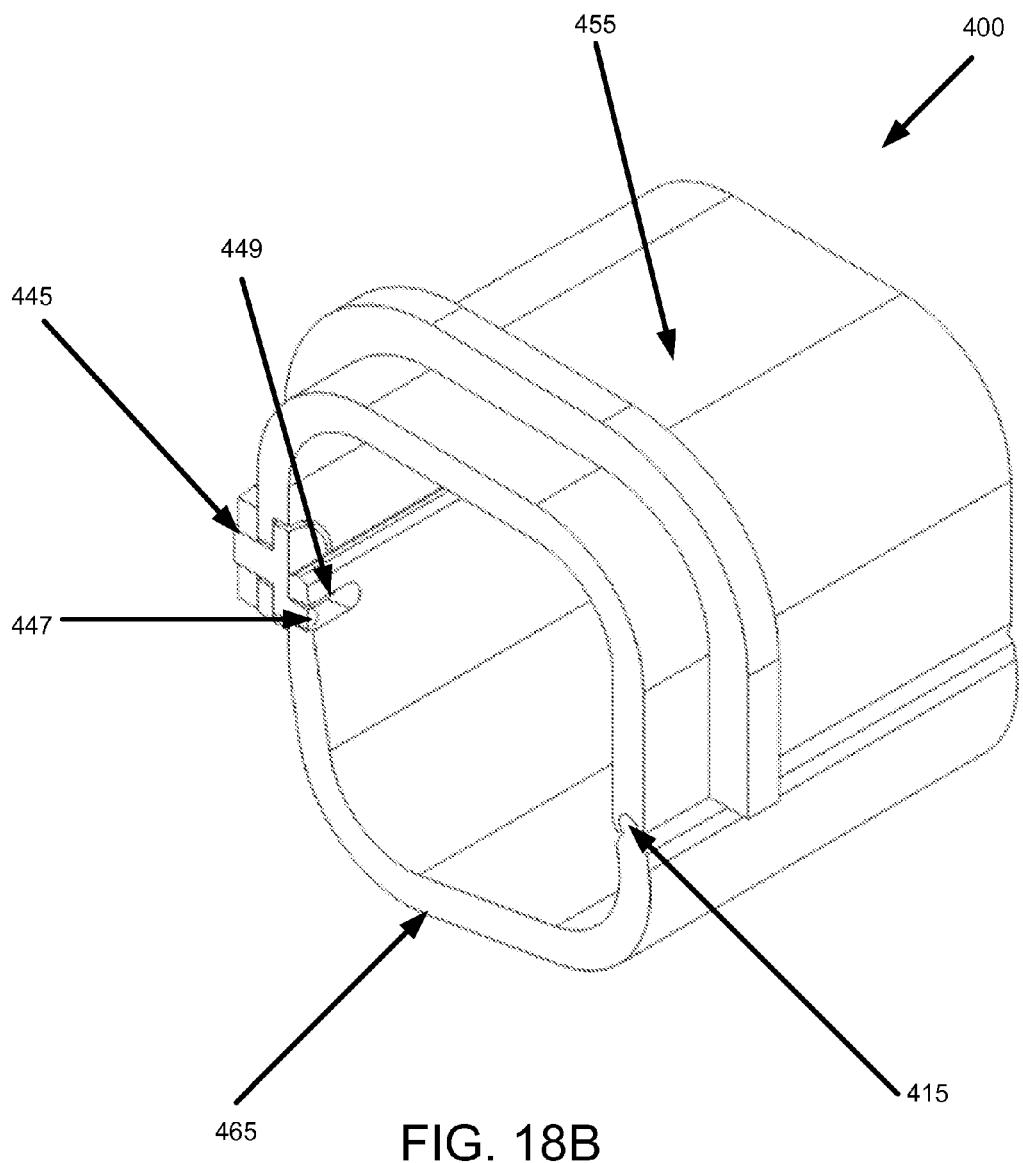
Figure 19:
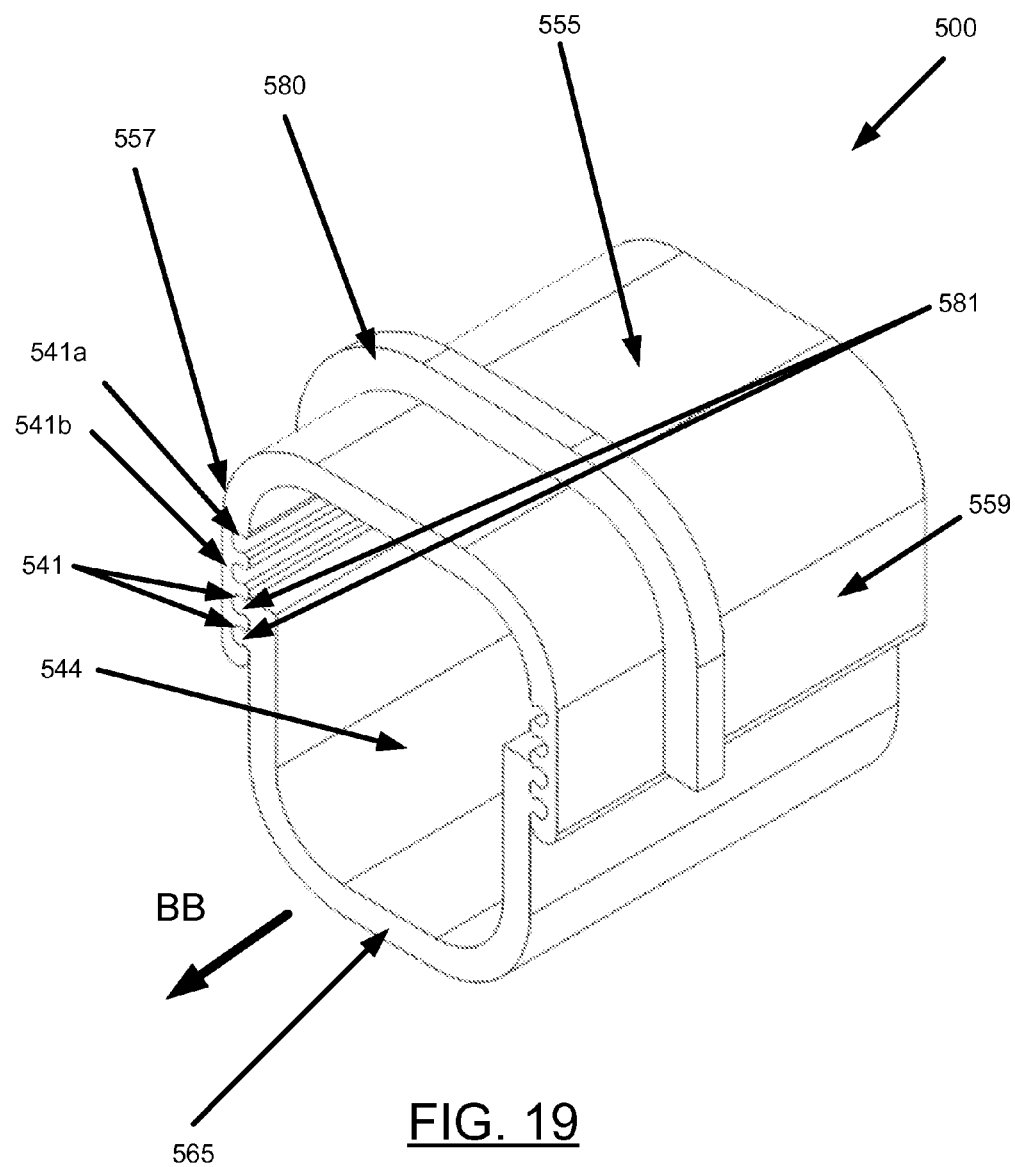
Figure 19A:
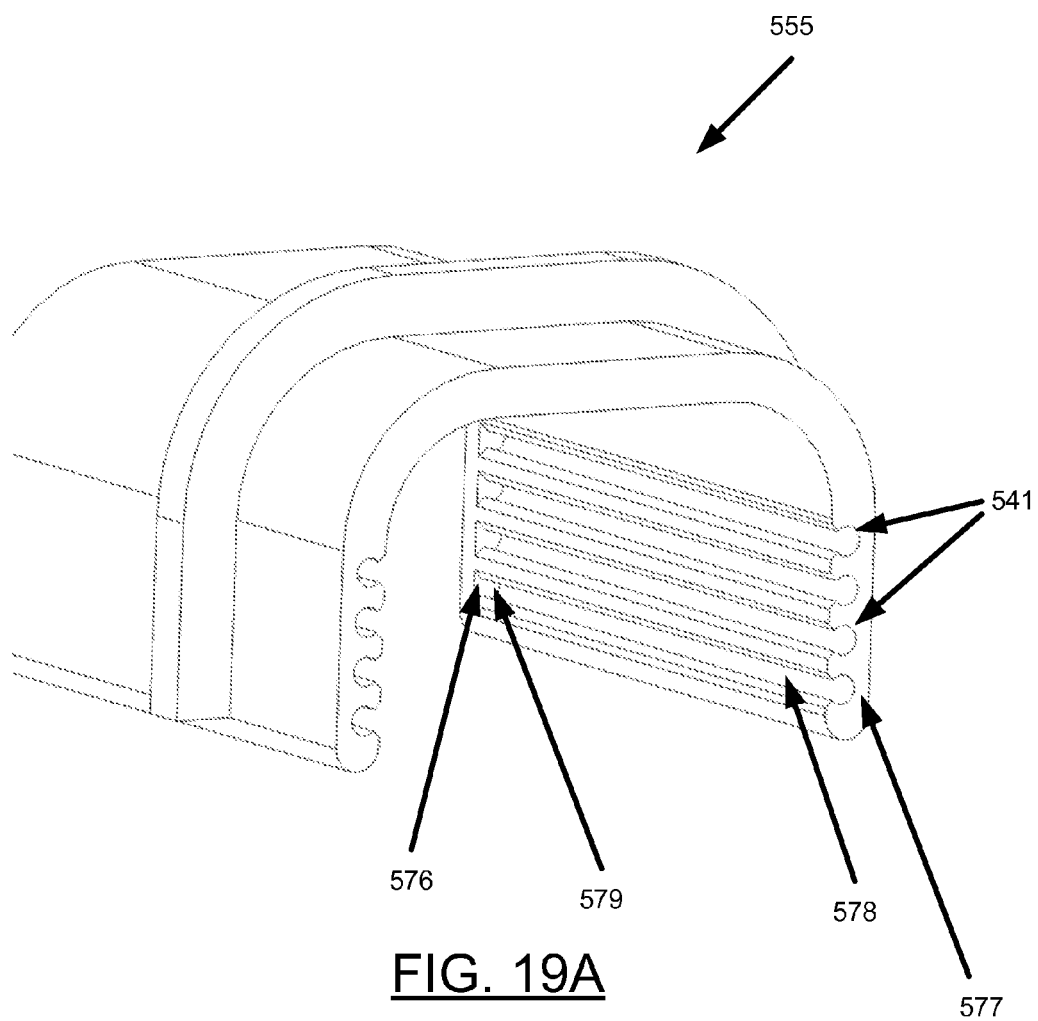

FIG. 8B is a detailed cross-sectional view taken along line 8B in FIG. 6 of the adjustable bite block shown in FIG. 6, wherein the adjustable bite block is disposed in a connected configuration, according to one embodiment of the present invention; and FIG. 9 is a detail view of a portion of the adjustable bite block shown in FIG. 7, wherein indicators of the radial dimension of the adjustable bite block are illustrated, according to some embodiments of the present invention;

FIG. 10 is a perspective view of an oral apparatus inserted into a person's mouth, wherein a strap is coupled to the oral apparatus, according to some embodiments of the present invention;

FIG. 11 is a perspective view of an oral apparatus inserted into a person's mouth, wherein a "Y" shaped strap is coupled to the oral apparatus, according to some embodiments of the present invention;

FIG. 12 is a perspective view of an oral appliance for maintaining a person's mouth in the open position, wherein the oral appliance is a wedge bite block, according to one embodiment of the present invention;

FIG. 13 is a side view of the wedge bite block shown in FIG. 12, according to one embodiment of the present invention;

FIG. 14 is a perspective view of a wedge bite block, wherein a handle extends from the wedge bite block, according to one embodiment of the present invention;

FIG. 15 is a perspective view of a dual wedge bite block, according to an additional embodiment of the present invention;

FIG. 16 is a perspective view of another example oral appliance for maintaining a person's mouth in an open position, wherein the oral appliance is an adjustable bite block, according to some example embodiments of the present invention;

FIG. 16A is a perspective view of a cross-section of the oral appliance shown in FIG. 16 taken along line 16A, according to some example embodiments of the present invention;

FIG. 17 is a perspective view of yet another example oral appliance for maintaining a person's mouth in an open position, wherein the oral appliance is an adjustable bite block, according to some example embodiments of the present invention;

FIG. 17A is a front view of a cross-section of the oral appliance shown in FIG. 17 taken along line 17A, according to some example embodiments of the present invention;

FIG. 18 is a perspective view of yet another example oral appliance for maintaining a person's mouth in an open position, wherein the oral appliance is an adjustable bite block, according to some example embodiments of the present invention;

FIG. 18A is a front view of the oral appliance shown in FIG. 18, according to some example embodiments of the present invention;

FIG. 18B is a perspective view of a cross-section of the oral appliance shown in FIG. 18 taken along line 18B, according to some example embodiments of the present invention;

FIG. 19 is a perspective view of another example oral appliance for maintaining a person's mouth in an open position, wherein the oral appliance is an adjustable bite block, according to some example embodiments of the present invention; and FIG. 19A is a perspective view of a top band of the oral appliance shown in FIG. 19, according to some example embodiments of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
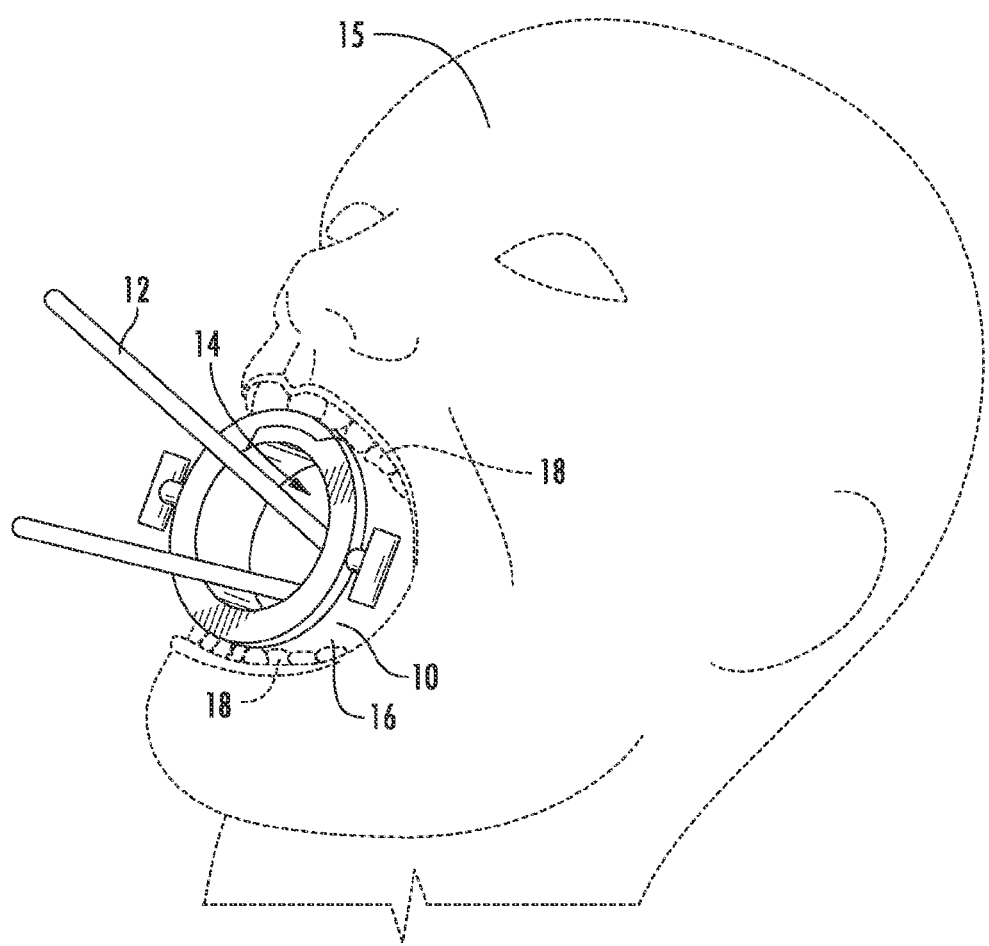
FIG. 1 is a perspective view illustrating an oral apparatus inserted into a person's mouth for maintaining their mouth in an open position, wherein instruments are being passed through the oral apparatus into the person's mouth, according to some embodiments of the present invention.

FIG. 1 shows a person 15 with an oral apparatus 10 positioned inside their mouth for maintaining their mouth open. The oral apparatus 10 can be useful in dental or medical procedures to allow medical instruments to pass into a person's mouth. During such procedures, the person may accidentally close their mouth, biting down on the instruments, thereby causing pain and/or injury to the person and possible damage to the medical instruments. Thus, the oral apparatus 10 is useful in maintaining the person's mouth in an open position and preventing that person from biting down during the procedure.

According to various embodiments, as shown in FIG. 1, the oral apparatus 10 fits within a person's mouth 16, inbetween their upper jaw and the lower jaw, and may rest on the person's teeth 18 (and/or gums). The oral apparatus 10 forces the upper and lower jaw apart so as to maintain the person's mouth 16 in the open position. In the depicted embodiment, the oral apparatus 10 is a bite block comprising at least one band that is curved. When connected, the band forms a closed loop with an opening 14 defined therethrough. The opening 14 may be large enough to allow medical instruments 12 to pass through it into the person's mouth 16 for performing a dental or medical procedure therein.

Additionally, as described in greater detail below with respect to specific embodiments, the oral apparatus 10 may be adjustable such that the closed loop of the band adjusts to different radial dimensions, corresponding to different sizes in the opening 14. Thus, the oral apparatus 10 may adjust to fit small or larger size mouths, as well as adjusting to fit differently sized medical instruments 12 that need to pass through the opening 14. Moreover, the oral apparatus 10 may be maneuvered into a different position in a person's mouth 16 to allow access into different portions of the person's mouth 16. For example, the oral apparatus 10 may be shifted to the left side of a person's mouth 16 to allow access for instruments 12 through the opening 14 to a person's right side of their mouth 16.

Figure 2:
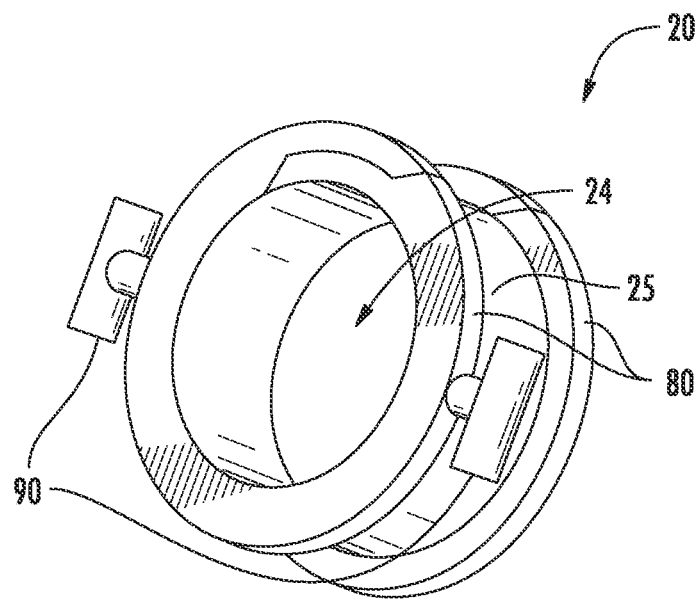
FIG. 2 is a perspective view of the oral appliance on FIG. 1, wherein the oral appliance is an adjustable bite block, according to one embodiment of the present invention.

FIG. 2 shows one embodiment of an adjustable bite block that incorporates a pull-snap mechanism. In the depicted embodiment, the adjustable bite block 20 comprises a band 25 that closes to form a generally annular shaped loop defining an opening 24.

Figure 3:
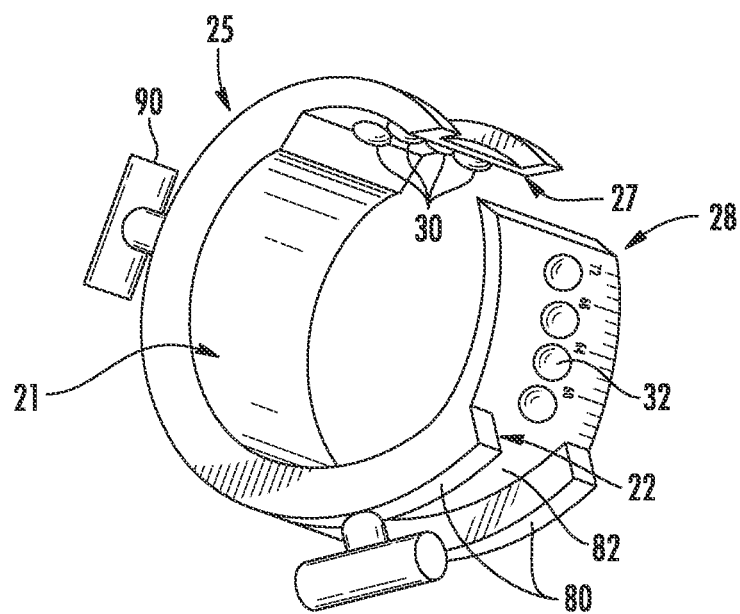
FIG. 3 is a perspective view of the adjustable bite block shown in FIG. 2 disposed in a disconnected configuration, according to one embodiment of the present invention.

When separated, the band 25, as shown in FIG. 3, is one elongated piece of curved material comprising a first end 27 and a second end 28. The first and second end 27, 28 are configured to be coupled to one another so as to define a closed loop (shown in FIG. 2) with the opening 24 defined therethrough. In the depicted embodiment, the band 25 comprises at least two tabs 30 and a receiving feature 32. The tabs 30 protrude from the band 25 near the first end 27 and are configured to engage with or "snap" into the receiving feature 32, which is located near the second end 28. Thus, when the receiving feature 32 engages with at least one tab 30, the band 25 forms a closed loop (shown in FIG. 5). With the band 25 in a closed loop, the adjustable bite block 20 can be placed into a person's mouth to hold the person's upper jaw and lower jaw open. In some embodiments, the band may comprise plastic material.

Additionally, the first and second ends 27, 28 of the band 25 are also configured to be selectively adjusted relative to one another to adjust a radial dimension of the closed loop. In the depicted embodiments of FIGS. 3-5, the band 25 of the adjustable bite block 20 comprises at least two tabs 30. The tabs 30 are spaced at different distances along the band 25 near the first end 27. The different distances of the tabs 30 along the band 25 correspond to different radial sizes of the closed loop and the opening 24. The greater the distance between the tab 30 and the first end 27, the smaller the closed loop and opening 24 will be when the receiving feature 32 near the second end 28 engages with that tab 30. Furthermore, the greater the overlap between the portion of the band 25 near the first end 27 and the portion of the band 25 near the second end 28, the smaller the closed loop.

As will be apparent to one of ordinary skill in the art, the band 25 may comprise more than two tabs (e.g., 3, 4, 8), and the number of tabs may correspond to the number of possible sizes of the closed loop. Additionally, the band 25 may comprise more than one receiving feature 32. For example, as shown in FIG. 3, the portion of the band 25 near the second end 28 may have receiving features 32 equal to the number of tabs 30 such that when the closed loop is the smallest radial dimension, all of the receiving features 32 engage individually with all of the tabs 30.

Figure 4:
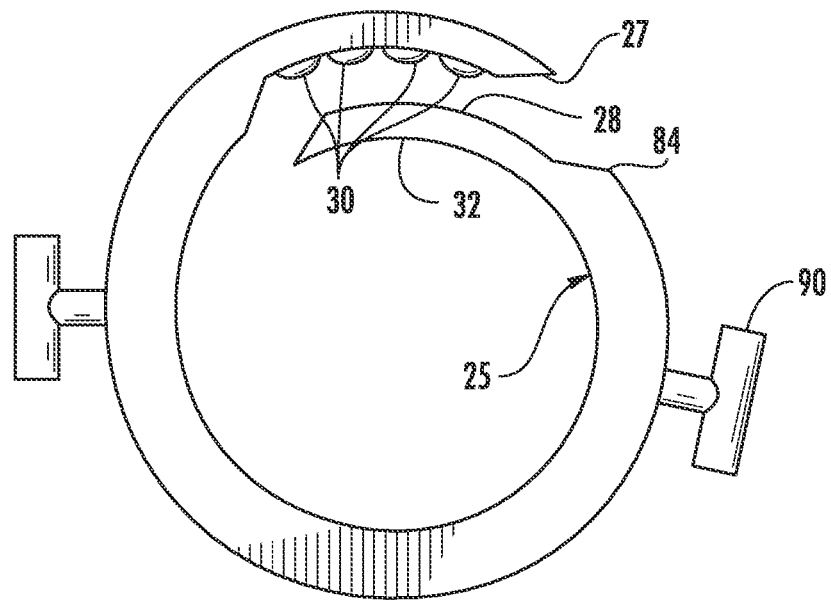
FIG. 4 is a side view of the adjustable bite block shown in FIG. 2 disposed in a disconnected configuration, according to one embodiment of the present invention.
Figure 5:
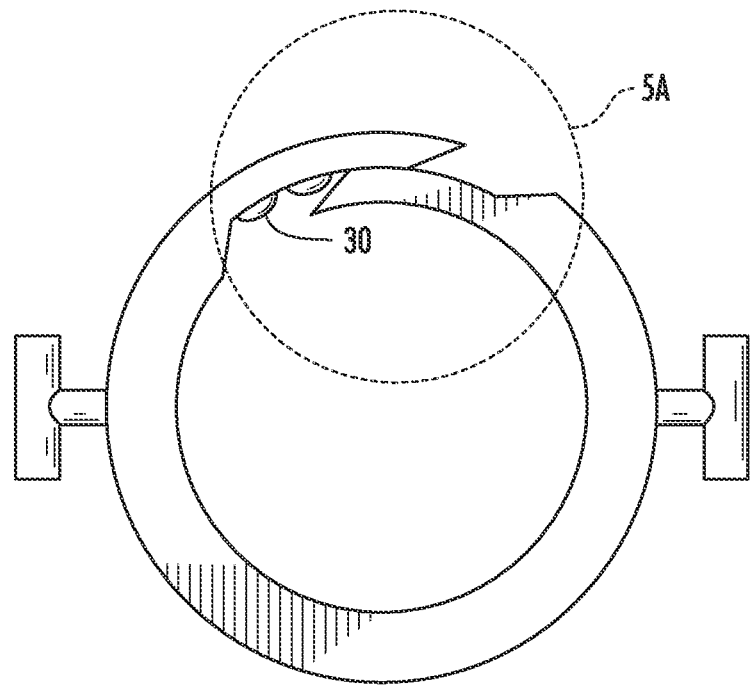
FIG. 5 is a side view of the adjustable bite block shown in FIG. 2 disposed in a connected configuration, according to one embodiment of the present invention.

With reference to FIGS. 3-5, to connect the first and second ends 27, 28 of the band 25 and close the loop, a user can connect or snap the receiving feature 32 over the tab 30. When in a closed loop, the band 25 comprises an interior side 21 facing inward and an exterior side 22 facing outward. In the depicted embodiment, the tabs 30 are located on the interior side 21 of the band 25. Thus, to connect the tabs 30 and receiving feature 32, a user passes the second end 28 of the band 25 under the first end 27 of the band 25 such that at least a portion of the portion of the first end 27 and at least a portion of the portion of the second end 28 overlap.

Once the band 25 is formed in a closed loop with at least one receiving feature 32 engaged with at least one tab 30, a user can disengage the receiving feature 32 and re-size the band 25. The user may pull the second end 28 of the band 25 away from the tabs 30 until the receiving feature 32 disengages with the tab 30. The receiving feature 32 near the second end 28 can then be placed onto or snapped into a different tab 30, such that the closed loop and opening 24 are re-sized to the desired radial dimension. In this way, the adjustable bite block 20 can be adjusted to fit the size of the person's mouth or the size of the medical instrument.

Figure 5A:
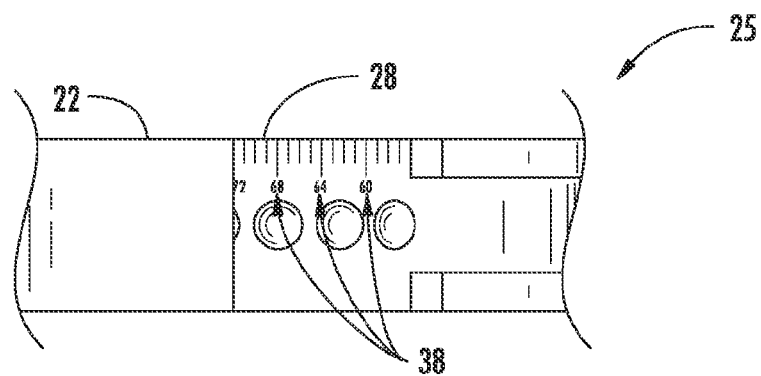
FIG. 5A is a detail view of a portion of the adjustable bite block shown in FIG. 5, wherein the radial dimension of the adjustable bite block in the connected position is indicated, according to one embodiment of the present invention.

To aid in determining the correct radial dimension of the adjustable bite block 20, indicators 38 can be placed on the band 25 to indicate to a user the size of the radial dimension being created. As shown in FIG. 5A, indicators 38 may be etches in the band 25 such as numbers or marks and may even correspond to mouth sizes for patients, such as 48Fr, 60Fr, 64Fr, 68Fr, 72Fr, or the like. Other measurement markers may also be used, such as diameter measurements. For example, in some embodiments, measurements indicating the minimum length required for an opening large enough for use of instruments may be indicated on the band.

Various embodiments of the oral apparatus may also include flanges or walls 80 configured to hold or hug a person's teeth to help maintain the oral apparatus 10 in the person's mouth. As shown in FIG. 3, the first band 25 of the adjustable bite block 20 may comprise at least one wall 80 that protrudes from the band 25. In the depicted embodiment, two walls 80 protrude from the exterior side 22 of the band 25 near the edges of the band 25 such that a gap or floor 82 exists between them. Such a configuration along the band 25 allows for a person's teeth to rest between the walls 80 on the floor 82. In other embodiments, the walls 80 or floor 82 may comprise cushioned material to provide comfort or protection for the person's mouth or teeth.

The wall 80 may extend any length along a portion of the band 25 up to the length of the exterior side 22 of the band 25 that corresponds to the smallest radial dimension. For example, with reference to FIG. 4, a portion of the second end 28 of the band 25 lays underneath a portion of the first end 27 of the band 25. Since the wall 80 protrudes from the exterior side 22 of the band 25, the wall 80 may only extend up to a point 84 which marks the end of the portion of the band 25 that will not be overlapped by the first end 27 of the band 25. A band 25 configured with the walls 80 extending to the point 84, as shown in FIG. 2, allows for most of the exterior side 22 of the band 25 to be covered by the walls 80, thereby ensuring maximum protection for keeping the adjustable bite block 20 from falling out of the person's mouth.

FIG. 6 shows another embodiment of an adjustable bite block that incorporates a pull-ratchet mechanism. In the depicted embodiment, the adjustable bite block 40 comprises a first band 55 and a second band 65 that connect to form a closed loop defining an opening 44. The first band 55, shown separate in FIG. 7, is an elongated piece of curved material comprising a first end 57 and a second end 59. The second band 65 also is an elongated piece of curved material comprising a first end 67 and a second end 69. In the depicted embodiment, the first and second bands 55, 65 each form general U-shapes. In some embodiments, the first and second bands may each comprise plastic material.

The first band 55 comprises an insert 53 located on a portion of the first band 55 near the first end 57. The second band 65 defines a slot 66 located at its second end 69 and configured to receive the insert 53 of the first band 55. In some embodiments, the second band 65 may further comprise an insert 63 on a portion near the first end 67 of the second band 65 and the first band 55 may further define a slot 56 located at its second end 59 and configured to receive the insert 63 of the second band 65.

With reference to FIG. 8A, which shows a cross-sectional view taken along line 8A in FIG. 7, the insert 63 of the second band 65 may comprise ratchet teeth 61. Additionally, the first band 55 may comprise ratchet receiving teeth 62 located near the second end 59 of the first band 55 and configured to engage with the ratchet teeth 61. Furthermore, the first band 55 may be configured to receive the insert 63 of the second band 65 through the slot 56 such that the ratchet teeth 61 on the insert 63 of the second band 65 engage with ratchet receiving teeth 62 of the first band 55. In various embodiments, the second band 65 may also comprise ratchet receiving teeth 62 located near the second end 69 and configured to engage with ratchet teeth 61 on the insert 53 of the first band 55. The second band 65 may also be configured to receive the insert 53 of the first band 55 through the slot 66 such that the ratchet teeth 61 on the insert 53 of the first band 55 engage with ratchet receiving teeth 62 of the second band 65.

With reference to FIG. 7, the insert 53 of the first band 55 is configured to insert into the slot 66 of the second band 65. Additionally, in the depicted embodiment, the insert 63 of the second band 65 is also configured to insert into the slot 56 of the first band 55. To close the loop, a user connects the first and second bands 55, 65 by placing the inserts 53, 63 into the slots 56, 66 and engaging the ratchet teeth 61 with the ratchet receiving teeth 62 (shown in FIG. 8B, which is a cross-sectional view taken along line 8B in FIG. 6).

The adjustable bite block 40, when connected, can form different radial dimensions for the closed loop and the opening 44. For example, as shown in the depicted embodiment of FIG. 7, each individual ratchet tooth 61 may be located at different distances along the inserts 53, 63 such that connection of different ratchet tooth 61 to the ratchet receiving teeth 62 corresponds to different radial dimensions of the closed loop and opening 44. The smaller the distance between the individual ratchet teeth 61 and the first end 57, 67 of the first and second bands 55, 65, the smaller the closed loop and opening 44 will be when the ratchet receiving feature 62 engages with the individual ratchet teeth 61. As will be apparent to one of skill in the art, the first and second bands 55, 65 may include any number of ratchet teeth 61 or ratchet receiving teeth 62, which may correspond to many different radial dimensions of the closed loop and opening 44.

Additionally, once the first and second bands 55, 65 are connected, they can be adjusted relative to one another to adjust the radial dimension of the closed loop and the opening 44. In depicted embodiments, the ratchet teeth 61 may be tapered to allow the loop to be expanded without allowing further insertion of the inserts 53, 63 or contraction of the radial dimension of the loop. The ratchet receiving teeth 62 may also comprise a similar taper. Such a taper allows a user to connect the first and second bands 55, 65 to create the smallest radial dimension loop and then adjust it by expanding the loop to the desired radial dimension. Also, the above described taper prevents contraction of the loop or opening 44, thereby preventing a person with the adjustable bite block 40 inserted in their mouth from biting down and altering the radial dimension. Tapers to ratchets, such as those described above, are known in the art for ratchet type designs.

To aid in determining the correct radial dimension of the adjustable bite block 40, indicators 48 can be placed on the inserts 53, 63 of the bands 55, 65 to indicate to a user the size of the radial dimension being created. As seen in FIG. 9, indicators 48 may be etches in the bands 55, 65 or inserts 53, 63 such as numbers or marks and may even correspond to mouth sizes for patients, such as 48Fr, 60Fr, 64Fr, 68Fr, 72Fr, or the like. Other measurements markers may also be used, such as diameter measurements.

As shown in FIGS. 6 and 7, the adjustable bite block 40 may also comprise at least one wall 80 for keeping the adjustable bite block 40 in a person's mouth. The first and second bands 55, 65 may comprise at least one flange or wall 80 protruding from generally exterior sides 91, 92, respectively. The walls 80 may extend along the length of each first and second band 55, 65 from the second end 59, 69 to the beginning of the insert 53, 63. As such, when the adjustable bite block 40 is formed into its smallest radial dimension, the ends of the walls 80 are adjacent to each other such that they form a closed loop. In the depicted embodiment, the first and second bands 55, 65 each comprise two walls 80 located near the edges of the bands such that a gap or floor 82 exists between them for a person's gums or teeth to rest on. In some embodiments, the walls 80 or floor 82 may comprise cushioned material to provide comfort or protection for the person's mouth or teeth.

In other various embodiments, the flanges or walls 80 may include indentations or slots for medical instruments to pass through. For example, such indentations or slots would allow additional instruments, like a suction tube, to pass into a person's mouth without taking up space in the opening 14 created by the oral apparatus 10.

As noted herein, some embodiments of the present invention contemplate other configurations for an oral appliance for maintaining a person's mouth open. Along these lines, some embodiments of the present invention contemplate other configurations for an adjustable bite block. Examples of some other contemplated adjustable bite blocks are illustrated in FIGS. 16, 16A, 17, 17A, 18, 18A, 18B, 19, and 19A.

FIG. 16 shows another example embodiment of an adjustable bite block that incorporates a ratchet mechanism. In the depicted embodiment, the adjustable bite block 240 comprises a first band 255 and a second band 265 that connect to form a closed loop defining an opening 244. With reference to FIG. 16A, the first band 255 is an elongated piece of curved material comprising a first end 257 and a second end 259. The first band 255 further defines an interior wall portion 258 near the second end 259. The second band 265 also is an elongated piece of curved material comprising a first end 267 and a second end 269. The second band 265 defines an interior wall portion 268 near the second end 269. In the depicted embodiment, the first and second bands 255, 265 each form general U-shapes. In some embodiments, the first and second bands may each comprise plastic material. Additionally, the adjustable bite block 240 may also comprise at least one wall 280 for keeping the adjustable bite block 240 in a person's mouth.

With reference to FIG. 16A, the first end 257 of the first band 255 may define one or more ratchet teeth 281. Additionally, the interior wall portion 258 of the first band 255 may comprise ratchet receiving teeth 282. Similarly, the first end 267 of the second band 265 may define one or more ratchet teeth 291. Additionally, the interior wall portion 268 of the second band 265 may comprise ratchet receiving teeth 292.

Furthermore, the second end 259 and the interior wall portion 258 of the first band 255 may be configured to receive the first end 267 of the second band 265 such that the ratchet teeth 291 of the second band 265 engage with ratchet receiving teeth 282 of the first band 255. Likewise, the second end 269 and the interior wall portion 268 of the second band 265 may be configured to receive the first end 257 of the first band 255 such that the ratchet teeth 281 of the first band 255 engage with ratchet receiving teeth 292 of the second band 265. In such a regard, the adjustable bite block 240, when connected, can form different radial dimensions for the closed loop and the opening 244. For example, as shown in the depicted embodiment of FIG. 16A, each the ratchet receiving teeth 282, 292 may each receive different ratchet teeth 281, 291 so as to define different radial dimensions of the closed loop and opening 244.

In order to resize the loop, a user may squeeze the second ends 259, 269 of the first and second bands 255, 265 in the horizontal direction (e.g., along arrows AA). By applying this pressure, the ratchet teeth 281, 291 and the corresponding ratchet receiving teeth 282, 292 may disengage and become spaced apart so as to enable relative vertical movement (and, thus, resizing of the loop).

Additionally, once the first and second bands 255, 265 are connected, they cannot be adjusted in the vertical direction such that biting down on the adjustable bite block 240 will resize the loop or opening 244. Said differently, the ratchet teeth 281, 291 and corresponding ratchet receiving teeth 282, 292 are designed with a taper to prevent adjustment from pressure in the vertical direction.

FIG. 17 shows another example embodiment of an adjustable bite block that incorporates an interference fit and hinge mechanism. In the depicted embodiment, the adjustable bite block 300 comprises a first band 355 and a second band 365 that connect to form a closed loop defining an opening 344. The first band 355 is an elongated piece of curved material comprising a first end 357 and a second end 359. The second band 365 also is an elongated piece of curved material comprising a first end 367 and a second end 369. The second end 359 of the first band 355 and the second end 369 of the second band 365 are hingedly connected at a hinge 315 that enables rotation of the second band 365 relative to the first band 355. In the depicted embodiment, the first and second bands 355, 365 each form general U-shapes. In some embodiments, the first and second bands may each comprise plastic material. Additionally, the adjustable bite block 300 may also comprise at least one wall 380 for keeping the adjustable bite block 300 in a person's mouth.

With reference to FIG. 17A, the second band 365 may define one or more protrusions 371 on a surface of the first end 367 facing the interior surface of the first end 357 of the first band 355. The first end 357 of the first band 355 may comprise at least one slot 341 configured to securely receive one of the protrusions 371 of the second band 365.

In order to define the radial dimension of the loop and the opening 344, the second band 365 may be rotated relative to the first band 355 such that a different protrusion 371 securely engages with the slot 341 of the first band 355. For example, a user could rotate the second band 365 downwardly to securely engaging a different protrusion 371a with the slot 341. In such a manner, the radial dimension of the loop and opening would enlarge. In some embodiments, additional space 342 may be defined within the first end 357 of the first band 355 to enable rotation of the second band 365. In such a manner, a user may define the radial dimension of the loop and the opening 344 of the adjustable bite block 300.

FIG. 18 shows another example embodiment of an adjustable bite block that incorporates a cam and hinge mechanism. In the depicted embodiment, the adjustable bite block 400 comprises a first band 455 and a second band 465 that connect to form a closed loop defining an opening 444. The first band 455 is an elongated piece of curved material comprising a first end 457 and a second end 459. The second band 465 also is an elongated piece of curved material comprising a first end 467 and a second end 469. The second end 459 of the first band 455 and the second end 469 of the second band 465 are hingedly connected at a hinge 415 that enables rotation of the second band 465 relative to the first band 455. In the depicted embodiment, the first and second bands 455, 465 each form general U-shapes. In some embodiments, the first and second bands may each comprise plastic material. Additionally, the adjustable bite block 400 may also comprise at least one wall 480 for keeping the adjustable bite block 400 in a person's mouth.

With reference to FIG. 18B, the first band 455 may define a knob 445 near the first end 457. The knob 445 is configured to rotate relative to the first band 455. The knob 445 may include a tab 447 that engages with an elongated slot 449 defined in the second band 465 near the first end 367 of the second band 465.

In order to define the radial dimension of the loop and the opening 444, the knob 445 may be rotated such that the tab 447 travels within the elongated slot 449 and forces the first end 469 of the second band 465 to move vertically relative to the first band 455. For example, a user could rotate the knob 445 clockwise to force the tab 447 (and, thus, the elongated slot 449) to travel upwardly. Such a motion would also cause the second band 465 to rotate upwardly. In such a manner, the radial dimension of the loop and opening would enlarge.

With reference to FIG. 18A, in some embodiments, a portion 478 of the second band 465 may be defined differently, such as to form a different shape (e.g., other than a U-shape). Along these lines, the second band 465 may define different shapes so as to provide for increased comfort within a user's mouth. For example, the shape of the second band 465 may define a bottom half of a hexagon. In such an embodiment, as the second band 465 is rotated relative to the first band 455, there may be more than one straight edge available to align with the bottom of the user's mouth.

FIG. 19 shows another example embodiment of an adjustable bite block that incorporates a shelving-type, interference fit mechanism. In the depicted embodiment, the adjustable bite block 500 comprises a first band 555 and a second band 565 that connect to form a closed loop defining an opening 544. The first band 555 is an elongated piece of curved material comprising a first end 557 and a second end 559. The second band 565 also is an elongated piece of curved material comprising a first end 567 and a second end 569. In the depicted embodiment, the first and second bands 555, 565 each form general U-shapes. In some embodiments, the first and second bands may each comprise plastic material. Additionally, the adjustable bite block 500 may also comprise at least one wall 580 for keeping the adjustable bite block 500 in a person's mouth.

The first band 555 may comprise at least two slots 541 positioned near the first end 557 and the second end 559. Additionally, in order to enable connection of the first band 555 and the second band 565, the second band 565 may define one or more protrusions 581 near the first end 567 and the second 569 that are configured to securely engage with one or more of the corresponding slots 541 of the first band 555.

In order to define the radial dimension of the loop and the opening 544, the second band 565 may be slide out of engagement with the first band 555 (e.g., along arrow BB). Then, depending on the desired radial dimension of the loop and opening 544, each protrusion 581 may be aligned with and slid into a corresponding slot 541. For example, the two protrusions 581 on each end of the second band 565 may be aligned (and then engaged) with the top two slots 541a, 541b in order to define a smaller opening 544 than that shown in FIG. 19.

With reference to FIG. 19A, in some embodiments, each slot 541 of the first band 555 may define an end stop 579 that prevents the protrusion 581 from being slid too far within the slot 541. Additionally or alternatively, in some embodiments, the cross-section 578 of each slot 541 may decrease from the front 577 to the back 576. In such a manner, a user may feel resistance as the protrusion 581 is slid along the slot 541, thereby further enhancing the interference fit of the protrusion 581 and slot 541.

FIG. 10 illustrates another embodiment of the present invention, wherein the oral apparatus 10 is configured to couple to a flexible strap 95 for holding the oral apparatus 10 in the person's mouth 16. Various embodiments of the oral apparatus 10, including previously described adjustable bite blocks 20, 40 may include at least one connector 90 protruding from the oral apparatus 10 and configured to couple to a strap 95. In the depicted embodiment, the oral apparatus 10 includes two radially opposite connectors 90 that are coupled to a strap 95 that is passed around the head of a person 15. As shown in FIG. 11, another embodiment of the oral apparatus 10 includes four connectors 90 spaced along the oral apparatus 10 to couple to a Y-shaped strap 96. The Y-shaped strap 96 is one flexible strap that forks into a "Y" before coupling to the connectors 90 on the oral apparatus 10. The "Y" allows for additional space 97 between the two forked straps coupled to the connectors 90 on the oral apparatus 10. The additional space 97 can be used to pass additional medical instruments 11', such as suction tubes, into the person's mouth 16 without utilizing the opening 14 created by the closed loop of the oral apparatus 10.

FIG. 12 shows another embodiment of an oral apparatus for maintaining a person's mouth open, wherein the oral apparatus is a wedge bite block. The wedge bite block 100 comprises an upper surface 110 and a lower surface 120. The upper surface 110 and lower surface 120 may be configured along differently angled planes so as to form a general wedge shape. In the depicted embodiment, the lower surface 120 lies along a flat plane in comparison to the slightly downward sloping plane of the upper surface 110 of the wedge bite block 100 (as shown in FIG. 13).

The wedge bite block 100 may also comprise at least one wedge wall 180. The wedge wall 180 protrudes from the upper or lower surface 110, 120 and is designed to engage with and lie adjacent to a person's teeth to maintain the wedge bite block 100 in place. In the depicted embodiment, the upper surface 110 comprises two walls 180 located near the edges of the upper surface 110 so as to create a gap or upper slot 115 between the walls 180 for fitting a person's upper gums or teeth. Additionally, the lower surface 120 also comprises two walls 180 spaced near the edges to create a lower slot 125 to engage and fit a person's lower gums or teeth.

The wedge bite block 100 can be inserted into a person's mouth to prop open and maintain open their mouth. For example, the wedge bite block 100 can be placed between a person's upper and lower teeth. The slight downward angle of the plane of the upper surface 110 will correspond to the angle at which a person's mouth will be maintained open. Thus, in order to increase the angle at which a person's mouth is open either the wedge bite block 100 can be inserted further into a person's mouth or the slope of the upper surface 110 can be increased. In other embodiments, the plane of the lower surface 120 can be given a slope in order to increase or decrease the angle at which a person's mouth is held open.

As shown in FIG. 14, other embodiments of a wedge bite block 100 may comprise a handle 130. The handle 130 protrudes from the wedge bite block 100 toward the outside of a person's mouth and is configured to allow a user (e.g., doctor, nurse, patient, etc.) to easily place and position the wedge bite block 100 in a person's mouth. The handle 130 also ensures that the user, who is placing the wedge bite block 100 into a person's mouth, will not accidentally or otherwise be harmed if the person bites down while the wedge bite block 100 is being placed into the person's mouth. In some embodiments, the handle 130 may comprise a grip 135 configured to allow a user to easily grab the handle 130.

FIG. 15 shows another embodiment of an oral apparatus for maintaining a person's mouth open, wherein the oral apparatus comprises two wedge bite blocks 100, 100'. The dual wedge bite block 200 comprises two wedge bite blocks 100, 100' configured to fit on either side of a person's mouth to maintain that person's mouth in the open position. In the depicted embodiment, the dual wedge bite block 200 also comprises a connection band 140 connecting the individual wedge bite blocks 100, 100'. In various embodiments, one or both of the wedge bite blocks 100, 100' may also comprise a handle 130 for easy placement and positioning of the dual wedge bite block 200.

Another embodiment of the present invention is a method for positioning an oral apparatus, such as any of the previously described apparatus embodiments, within a person's mouth. In another embodiment, the method comprises providing at least one band of curved material comprising a first portion and a second portion, coupling the first and second portions to one another so as to define a closed loop with an opening defined therethrough, and positioning the bite block within a person's mouth such that at least a portion of the loop engages the person's teeth to maintain the person's mouth in an open position. The method may further comprise adjusting the first and second portions relative to one another so as to adjust a radial dimension of the loop prior to the coupling step. The method may also further comprise inserting an instrument through the opening defined in the loop while the bite block is positioned within the person's mouth.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included herein. Although specific terms are employed herein, they are used in a generic and descriptive sense only and not for purposes of limitation.

The invention claimed is:

1. An adjustable bite block for positioning within a person's mouth and maintaining the mouth in an open position, the adjustable bite block comprising:

at least one band of curved material comprising a first portion and a second portion, the first and second portions configured to be coupled to one another so as to define a closed loop with an opening defined therethrough, wherein the first and second portions are further configured to be selectively adjusted relative to one another so as to adjust a radial dimension of the loop, and wherein the band is configured to be positioned within the person's mouth such that at least a portion of the loop maintains the person's mouth in an open position, wherein the first portion defines at least two slots of different heights, wherein the second portion defines at least one protrusion, and wherein each slot is configured to receive the at least one protrusion to define a radial dimension of the opening.

2. The adjustable bite block of claim 1, wherein the at least one protrusion of the second portion is configured to be slidably removed from the at least one slot of the first portion and repositioned into a different at least one slot of the first portion to define a different radial dimension of the opening.

3. The adjustable bite block of claim 1 further comprising at least one wall configured for keeping the adjustable bite block in a person's mouth.

4. The adjustable bite block of claim 3, wherein the at least one wall extends radially from the first portion of the at least one band.

5. The adjustable bite block of claim 1, wherein each slot comprises an end stop configured to prevent a respective protrusion from being slid past a predetermined point within the respective slot.

6. The adjustable bite block of claim 1, wherein each slot defines a cross-sectional dimension that decreases from a front part of a respective slot to a back part of the respective slot such that a resistance to engagement of a respective protrusion within the respective slot increases as the respective protrusion is slid further into the respective lot.

* * * * *